United States Patent [19]

Lee et al.

[11] Patent Number: 5,491,172
[45] Date of Patent: Feb. 13, 1996

[54] N-ACYL SULFAMIC ACID ESTERS (OR THIOESTERS), N-ACYL SULFONAMIDES, AND N-SULFONYL CARBAMIC ACID ESTERS (OR THIOESTERS) AS HYPERCHOLESTEROLEMIC AGENTS

[75] Inventors: Helen T. Lee, Ann Arbor; Joseph A. Picard; Drago R. Sliskovic, both of Ypsilanti; Wendell Wierenga, Ann Arbor, all of Mich.

[73] Assignee: Warner-Lambert Company, Morris Plains, N.J.

[21] Appl. No.: 223,932

[22] Filed: Apr. 13, 1994

Related U.S. Application Data

[63] Continuation-in-part of Ser. No. 62,515, May 14, 1993, abandoned.

[51] Int. Cl.⁶ .......................... A61K 31/18; C07C 307/02
[52] U.S. Cl. ............................ 514/602; 514/605; 560/12
[58] Field of Search ............................ 560/12; 514/602, 514/605

[56] References Cited

U.S. PATENT DOCUMENTS

| | | | |
|---|---|---|---|
| 3,377,375 | 4/1968 | Stephens | 560/12 |
| 3,560,563 | 2/1971 | Childress . | |
| 3,622,626 | 11/1971 | Moore . | |
| 3,833,608 | 9/1974 | Rooney et al. | 514/419 |
| 5,053,072 | 10/1991 | Ort et al. | 71/92 |
| 5,085,684 | 2/1992 | Müller et al. | 71/92 |
| 5,091,392 | 2/1992 | Raddatz et al. | 514/311 |
| 5,157,122 | 10/1992 | Hughes et al. | 546/176 |
| 5,186,736 | 2/1993 | Ort et al. | 504/225 |
| 5,190,968 | 3/1993 | Gillard et al. | 514/419 |
| 5,245,068 | 9/1993 | Picard et al. | 560/12 |
| 5,250,558 | 10/1993 | Chakravarty et al. | 514/383 |
| 5,254,589 | 10/1993 | Picard | 514/592 |
| 5,324,710 | 6/1994 | Ort et al. . | |

FOREIGN PATENT DOCUMENTS

| | | |
|---|---|---|
| 399818A1 | 11/1990 | European Pat. Off. . |
| 400974A2 | 12/1990 | European Pat. Off. . |
| 409332A2 | 1/1991 | European Pat. Off. . |
| 499926A1 | 8/1991 | European Pat. Off. . |
| 461040 | 12/1991 | European Pat. Off. . |
| 0467183 | 1/1992 | European Pat. Off. . |
| 0467183A1 | 1/1992 | European Pat. Off. . |
| 0507171A1 | 10/1992 | European Pat. Off. . |
| 0507171 | 10/1992 | European Pat. Off. ........ 249/12 |
| 3935277 | 10/1989 | Germany . |
| 47-20139 | 9/1972 | Japan . |
| 2263637 | 8/1993 | United Kingdom . |
| 2263635 | 8/1993 | United Kingdom . |
| 2263638 | 8/1993 | United Kingdom . |
| 2263639 | 8/1993 | United Kingdom . |
| 9111999 | 8/1991 | WIPO . |
| 9115209 | 10/1991 | WIPO . |
| 92/01675 | 2/1992 | WIPO . |
| 92/08692 | 5/1992 | WIPO . |
| 92/07826 | 5/1992 | WIPO . |
| 9216511 | 10/1992 | WIPO ........ 239/52 |
| 93/10086 | 5/1993 | WIPO . |

OTHER PUBLICATIONS

W. H. Daly, et al., *J Org Chem*, 1974, 39:11, 1597–1600.
W. J. Spillane, et al., *J Syn Org Chem*, 1986, 12:1021–1024.
J. Zinczuk, et al., *J Het Chem*, 1992, 29:4, 859–866.
D. Sliskovic, et al, *J Med Chem*, 1994, 37:560–562.
A. Warm, et al., *J Org Chem*, 1994, 59:13, 3540–3542.

*Primary Examiner*—José G. Dees
*Assistant Examiner*—Joseph M. Conrad
*Attorney, Agent, or Firm*—Elizabeth M. Anderson

[57] ABSTRACT

The present invention is directed to compounds useful for the regulation of cholesterol of Formula I, methods for using them and pharmaceutical compositions thereof,

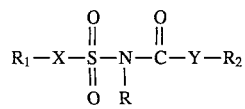

wherein X and Y are oxygen, sulfur, or $(CR'R'')_n$ wherein n is 1 to 4; R is hydrogen, alkyl, or benzyl; $R_1$ and $R_2$ are phenyl, substituted phenyl, naphthyl, substituted naphthyl, an aralkyl group, an alkyl chain, adamantyl, or a cycloalkyl group.

17 Claims, No Drawings

N-ACYL SULFAMIC ACID ESTERS (OR THIOESTERS), N-ACYL SULFONAMIDES, AND N-SULFONYL CARBAMIC ACID ESTERS (OR THIOESTERS) AS HYPERCHOLESTEROLEMIC AGENTS

This is a continuation-in-part of U.S. Ser. No. 08/062,515 filed May 14, 1993, now abandoned.

BACKGROUND OF INVENTION

This invention relates to chemical compounds having pharmacological activity, to pharmaceutical compositions which include these compounds, and to a pharmaceutical method of treatment. More particularly, this invention concerns certain N-acyl sulfamic acid esters (or thioesters), N-acyl sulfonamides, and N-sulfonyl carbamic acid esters (or thioesters) which inhibit the enzyme, acyl-coenzyme A:cholesterol acyltransferase (ACAT), pharmaceutical compositions containing these compounds, and a method of treating hypercholesterolemia and atherosclerosis.

The compounds of the instant invention show increased chemical stability over those of U.S. Pat. No. 5,245,068.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme, acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention is directed to compounds of Formula I below, methods for using the compounds of Formula I, pharmaceutical compositions thereof, and processes for preparing the compounds.

The first aspect of the invention is a compound of Formula I

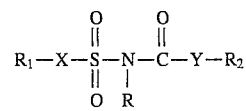

or a pharmaceutically acceptable salt thereof wherein:

X and Y are selected from oxygen, sulfur and $(CR'R'')_n$, wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl; with the proviso that at least one of X and Y is $—(CR'R'')_n—$ and with the further proviso when X and Y are both $(CR'R'')_n$ and R' and R'' are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from
 (a) phenyl or phenoxy each of which is unsubstituted or is substituted with 1 to 5 substituents selected from
  phenyl,
  an alkyl group having from 1 to 6 carbon atoms and which is straight or branched,
  an alkoxy group having from 1 to 6 carbon atoms and which is straight or branched;
  phenoxy,
  hydroxy,
  fluorine,
  chlorine,
  bromine,
  nitro,
  trifluoromethyl,
  —COOH,
  —COOalkyl wherein alkyl has from 1 to 4 carbon atoms and is straight or branched,
  $—(C_2)_p NR_3 R_4$ wherein p is zero or one, and each of $R_3$ and $R_4$ is selected from hydrogen or a straight or branched alkyl group having 1 to 4 carbon atoms;
 (b) 1- or 2-naphthyl unsubstituted or substituted with from 1 to 3 substituents selected from
  phenyl,
  an alkyl group having from 1 to 6 carbon atoms and which is straight or branched,
  an alkoxy group having from 1 to 6 carbon atoms and which is straight or branched;
  hydroxy,
  phenoxy,
  fluorine,
  chlorine,
  bromine,
  nitro,
  trifluoromethyl,
  —COOH,
  —COOalkyl wherein alkyl has from 1 to 4 carbon atoms and is straight or branched,
  $—(CH_2)_p NR_3 R_4$ wherein p, $R_3$ and $R_4$ have the meanings defined above;
 (c) arylalkyl;
 (d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms; with the provisos:

(i) where X is $(CH_2)_n$, Y is oxygen, and $R_1$ is a substituted phenyl, then $R_2$ is a substituted phenyl;

(ii) where Y is oxygen X is $(CH_2)_n$, $R^2$ is phenyl or naphthyl, then $R^1$ is not a straight or branched alkyl chain; and (iii) the following compounds are excluded:

| X | Y | R | $R_1$ | $R_2$ |
|---|---|---|---|---|
| $CH_2$ | O | H | $(CH_2)_2CH_3$ | Ph |
| $CH_2$ | O | H | $CH_3$ | Ph |
| $CH_2$ | O | H | 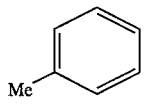 | i-Pr. |

Preferred compounds of the instant invention are those of Formula I:

wherein $R_1$ is phenyl or is phenyl disubstituted in the 2,6-positions, wherein $R_2$ is phenyl or is phenyl disubstituted in the 2,6-positions, wherein each of $R_1$ and $R_2$ is phenyl, wherein each phenyl is disubstituted in the 2,6-position, wherein $R_1$ is phenyl disubstituted in the 2,6-positions and $R_2$ is phenyl trisubstituted in the 2,4,6-positions, wherein $R_1$ is 2,6-bis(1-methylethyl)phenyl and $R_2$ is 2,6-bis(1-methylethyl)phenyl or 2,4,6-tris(1-methylethyl)phenyl, wherein one of $R_1$ and $R_2$ is the group

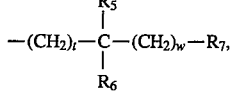

wherein t is zero or 1 to 4; w is zero or 1 to 4 with the proviso that the sum of t and w is not greater than 5; $R_5$ and $R_6$ are each independently selected from hydrogen or alkyl having from 1 to 6 carbon atoms, or when $R_5$ is hydrogen, $R_6$ can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_p NR_3 R_4$ wherein P, $R_3$ and $R_4$ have the meanings defined above.

Also preferred compounds of the instant invention are those of Formula I wherein X is oxygen, sulfur or $(CR'R'')_n$;

Y is oxygen, sulfur or $(CR'R'')_n$, with the proviso that at least one of X or Y is $(CR'R'')_n$ wherein n is an integer of from 1 to 4 and R' and R'' are each independently hydrogen, straight or branched alkyl of from 1 to 6 carbons, optionally substituted phenyl, halogen, hydroxy, alkoxy, acyloxy, cycloalkyl, or R' and R'' taken together form a carbonyl or a spirocycloalkyl group of from 3 to 10 carbons;

R is hydrogen;

$R_1$ is phenyl optionally substituted, straight or branched alkyl of from 1 to 10 carbon atoms, cycloalkyl of from 3 to 10 carbon atoms;

$R_2$ is phenyl optionally substituted, straight or branched alkyl of from 1 to 10 carbon atoms, cycloalkyl of from 3 to 8 carbon atoms, phenoxy optionally substituted with the proviso that only if X is $(CR'R'')_n$ can $R_1$ be optionally substituted phenoxy and only if Y is $(CR'R'')_n$ can $R_2$ be optionally substituted phenoxy, and with the further proviso that at least one of $R_1$ and $R_2$ is optionally substituted phenyl or phenoxy.

More preferred compounds of the instant invention are those of Formula I wherein X is oxygen;

Y is $(CR'R'')_n$ wherein n is an integer of from 1 to 2;

R is hydrogen;

$R_1$ is optionally substituted phenyl;

$R_2$ is optionally substituted phenyl or phenoxy, straight or branched alkyl of from 1 to 10 carbons, or cycloalkyl of from 3 to 10 carbons; and R' and R'' are each independently hydrogen, straight or branched alkyl of from 1 to 6 carbons, optionally substituted phenyl, halogen, hydroxy, alkoxy, acyloxy, cycloalkyl, or R' and R'' taken together form a carbonyl or a spirocycloalkyl.

The present invention also provides a pharmaceutical composition for regulating plasma cholesterol concentrations comprising a therapeutically effective amount of one or more compounds of Formula I. It further provides a method of treating hypercholesterolemia and for treating atherosclerosis comprising administering to a patient an effective amount of one or more compounds of Formula I with a pharmaceutically acceptable carrier.

DETAILED DESCRIPTION OF THE INVENTION

The compounds of the present invention provide a novel class of N-acyl sulfamic acid esters (or thioesters), N-acyl sulfonamides, and N-sulfonyl carbamic acid esters (or thioesters) which are ACAT inhibitors, rendering them useful in treating hypercholesterolemia and atherosclerosis.

In Formula I above, illustrative examples of straight or branched saturated hydrocarbon chains having from 1 to 20 carbon atoms include methyl, ethyl, n-propropyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative examples of straight or branched alkyl groups having from 1 to 6 carbon atoms as used in Formula I include methyl, ethyl, n-propyl, isopropyl, n-pentyl, n-butyl, and tert-butyl.

Illustrative examples of cycloalkyl groups, as used in Formula I, include cyclopentyl, cyclohexyl, cyclooctyl, tetrahydronaphthyl, and 1- or 2-adamantyl.

Spirocycloalkyl groups are, for example, spirocyclopropyl, spirocyclobutyl, spirocyclopentyl, and spirocyclohexyl.

Illustrative examples of arylalkyl groups are: benzyl, phenethyl, 3-phenylpropyl, 2-phenylpropyl, 4-phenylbutyl, 2-phenylbutyl, 3-phenylbutyl, benzhydryl, 2,2-diphenylethyl, and 3,3-diphenylpropyl.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Berge SN, et al, *J Pharm Sci* 1977;66:1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Preferred compounds of the present invention are those wherein one of $R_1$ and $R_2$ is phenyl, and more preferably wherein one of $R_1$ and $R_2$ is substituted phenyl, and still more preferably wherein one of $R_1$ and $R_2$ is phenyl disubstituted in the 2,6-positions.

In one preferred embodiment both $R_1$ and $R_2$ are phenyl disubstituted in the 2,6-positions. In another preferred embodiment $R_1$ is phenyl disubstituted in the 2,6-position and $R_2$ is trisubstituted in the 2,4,6-positions.

In another preferred embodiment of the present invention, $R_1$ is 2,6-bis(1-methylethyl)phenyl; and $R_2$ is 2,6-bis(1-methylethyl)phenyl or 2,4,6-tris(1-methylethyl)phenyl.

Preferred compounds of Formula I include, but are not limited to the following:

Sulfamic acid (phenylacetyl)-2,6-bis(1-methylethyl)phenyl ester,

Sulfamic acid [[2,4,6-tris(1-methylethyl)phenyl]acetyl-2,6-bis(1-methylethyl)phenyl ester, Sulfamic acid[[2,6-bis(1-methylethyl)phenyl]acetyl]-2,6-bis(1-methylethyl)phenyl ester, Sulfamic acid [[2,4,6-tris(1-methylethyl)phenyl]acetyl-2,4,6-tris(1-methylethyl)phenyl ester, Sulfamic acid [[2,6-bis(1-methylethyl)phenyl]acetyl]-2,4,6-tris(1-methylethyl)phenyl ester, Sulfamic acid[adamantaneacetyl]-2,6-bis[1-methylethyl)phenyl ester Sulfamic acid[[2,6-bis(1-methylethyl)phenyl]acetyl]-2,6-bis(1-methylethyl)phenyl ester-sodium salt, Sulfamic acid[[2,4,6-tris(1-methylethyl)phenyl]acetyl]-2,6-bis(1-methylethyl)phenyl ester-sodium salt, Sulfamic acid (decanoyl)-2,6-bis-(1-methylethyl)phenyl ester, Sulfamic acid (dodecanoyl)-2,6-bis-(1-methylethyl)phenyl ester, 2,6-Bis(1-methylethyl)-N-[[[2,4,6-tris(1-methylethyl)phenyl]methyl]sulfonyl]benzeneacetamide, 2,6-Bis(1-methylethyl)-N-[[[2,4,6-tris(1-methylethyl)phenyl]methyl]sulfonyl]benzeneacetamide-sodium salt, 2,6-Bis(1-methylethyl)phenyl[[[2,4,6-tris(1-methylethyl)phenyl]methyl]sulfonyl]carbamate, 2,6-Bis(1-methylethyl)phenyl[[[2,4,6-tris(1-methylethyl)phenyl]methyl]sulfonyl]carbamate-sodium salt, Sulfamic acid (1-oxo-3,3-diphenylpropyl)-2,6-bis(1-methylethyl)phenyl ester, Sulfamic acid [2,6-dichlorophenyl(acetyl)]-2,6-bis(1-methylethyl)phenyl ester, Sulfamic acid [2,6-dichlorophenyl(acetyl)]-2,6-bis(1-methylethyl)phenyl ester, Sulfamic acid trans-[(2-phenylcyclopropyl)-carbonyl]-2,6-bis(1-methylethyl)phenyl ester, Sulfamic acid [2,5-dimethoxyphenyl(acetyl)]-2,6-bis(1-methylethyl)phenyl ester, Sulfamic acid [2,4,6-trimethoxyphenyl(acetyl)]-2,6-bis(1-methylethyl)phenyl ester, Sulfamic acid [2,4,6-trimethylphenyl(acetyl)]-2,6-bis(1-methylethyl)phenyl ester, Sulfamic acid [2-thiophenyl(acetyl)]-2,6-bis(1-methylethyl)phenyl ester, Sulfamic acid [3-thiophenyl(acetyl)]-2,6-bis(1-methylethyl)phenyl ester, Sulfamic acid [2-methoxyphenyl(acetyl)]-2,6-bis(1-methylethyl)phenyl ester, Sulfamic acid (oxophenylacetyl)-2,6-bis(1-methylethyl)phenyl ester, Sulfamic acid [2-trifluoromethylphenyl(acetyl)]-2,6-bis(1-methylethyl)phenyl ester, Sulfamic acid (1-oxo-2-phenylpropyl)-2,6-bis(1-methylethyl)phenyl ester, Sulfamic acid (cyclopentylphenylacetyl)-2,6-bis(1-methylethyl)phenyl ester, Sulfamic acid (cyclohexylacetyl)-2,6-bis(1-methylethyl)phenyl ester, Sulfamic acid (diphenylacetyl)-2,6-bis(1-methylethyl)phenyl ester, Sulfamic acid (triphenylacetyl)-2,6-bis(1-methylethyl)phenyl ester, Sulfamic acid [(1-phenylcyclopentyl)carbonyl]-2,6-bis(1-methylethyl)phenyl ester, Sulfamic acid (3-methyl-1-oxo-2-phenylpentyl)-2,6-bis(1-methylethyl)phenyl ester, Sulfamic acid (1-oxo-2-phenylbutyl)-2,6-bis(1-methylethyl)phenyl ester, Sulfamic acid (cyclohexylphenylacetyl)-2,6-bis(1-methylethyl)phenyl ester, Sulfamic acid (1-oxo-2,2-diphenylpropyl)-2,6-bis(1-methylethyl)phenyl ester, Sulfamic acid [(9H-fluoren-9-yl)carbonyl]-2,6-bis(1-methylethyl)phenyl ester, Sulfamic acid (1-oxo-3-phenylpropyl)-2,6-bis(1-methylethyl)phenyl ester, Sulfamic acid [1-oxo-3-[2,4,6-tris(1-methylethyl)phenyl]-2-propenyl]-2,6-bis(1-methylethyl)phenyl ester, Sulfamic acid [1-oxo-3-[2,4,6-tris(1-methylethyl)phenyl]propyl]-2,6-bis(1-methylethyl)phenyl ester, Sulfamic acid [(acetyloxy)[2,4,6-tris(1-methylethyl)phenyl]acetyl]-2,6-bis(1-methylethyl)phenyl ester, Sulfamic acid [hydroxy[2,4,6-tris(1-methylethyl)phenyl]acetyl]-2,6-bis(1-methylethyl)phenyl ester, Sulfamic acid [fluoro[2,4,6-tris(1methylethyl)phenyl]acetyl]-2,6-bis(1-methylethyl)phenyl ester, Sulfamic acid (3-methyl-1-oxo-2-phenylpentyl)-2,6-bis(1-methylethyl)phenyl ester sodium salt, Sulfamic acid [[2,4,6-tris(1-methylethyl)phenoxy]acetyl]-2,6-bis(1-methylethyl)phenyl ester, Sulfamic acid [[2,6-bis(1-methylethyl)phenoxy]acetyl]-2,6-bis(1-methylethyl)phenyl ester, and Sulfamic acid [[2,4,6-tris(1-methylethyl)phenyl]acetyl]-2,6-bis(phenyl)phenyl ester.

As shown by the data presented below in Table 1, the compounds of the present invention are inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field FJ, Salone RG, *Biochemica et Biophysica*, 1982;712:557–570. The test assesses the ability of a test compound to inhibit the acylation of cholesterol by oleic acid by measuring the amount of radiolabeled cholesterol oleate formed from radiolabeled oleic acid in a tissue preparation containing rat liver microsomes.

The data appear in Table 1 where they are expressed in $IC_{50}$ values; i.e., the concentration of test compound required to inhibit the activity of the enzyme by 50%.

TABLE 1

| Example | LAI $IC_{50}$ (μM) |
|---|---|
| 1 | 9.7 |
| 2 | 12 |
| 3 | 11 |
| 4 | 13 |
| 5 | 12 |
| 6 | 12 |
| 7 | 47 |
| 8 | 21 |
| 10 | >5 |
| 11 | >10 |
| 13 | 25 |
| 14 | 33 |
| 15 | 34 |
| 16 | 36 |
| 17 | >50 |
| 18 | 22 |
| 19 | >50 |
| 20 | >50 |
| 21 | 55 |
| 22 | 50 |

TABLE 1-continued

| Example | LAI $IC_{50}$ (μM) |
|---|---|
| 23 | 12 |
| 24 | 26 |
| 25 | 7.2 |
| 26 | 28 |
| 27 | 12 |
| 28 | 6 |
| 29 | 15 |
| 30 | 4.1 |
| 31 | 3.3 |
| 32 | 8.9 |
| 33 | 9.3 |
| 34 | 7.7 |
| 35 | 8.9 |
| 36 | 22 |
| 37 | 16 |
| 38 | 31 |
| 39 | 32 |
| 40 | 32 |
| 41 | 28 |
| 42 | 7 |
| 43 | 31 |
| 44 | 9.4 |
| 45 | 5.6 |
| 46 | 34 |
| 47 | 38 |
| 48 | 8.3 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet (designated PCC) containing 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Compound of Example | % Change (mg/dl) |
|---|---|
| 1 | −63 |
| 2 | −62 |
| 3 | −79 |
| 4 | −47 |
| 5 | −73 |
| 6 | −75 |
| 7 | −17 |
| 8 | −66 |
| 10 | −26 |
| 11 | −8 |
| 12 | −5 |
| 13 | −31 |
| 14 | −12 |
| 15 | −14 |
| 16 | +10 |
| 17 | −40 |
| 18 | −47 |
| 19 | −20 |
| 20 | −19 |
| 21 | −16 |
| 22 | −23 |
| 23 | −19 |
| 24 | −24 |
| 25 | −71 |
| 26 | −26 |

TABLE 2-continued

| Compound of Example | % Change (mg/dl) |
|---|---|
| 27 | −72 |
| 28 | −30 |
| 29 | −9 |
| 30 | −40 |
| 31 | −30 |
| 32 | −48 |
| 33 | −63 |
| 34 | −67 |
| 35 | −9 |
| 36 | −6 |
| 37 | −50 |
| 38 | −16 |
| 39 | +5 |
| 40 | −54 |
| 41 | −73 |
| 42 | −25 |
| 43 | −45 |
| 44 | −74 |
| 45 | −63 |
| 46 | −57 |
| 47 | −46 |
| 48 | −73 |

In therapeutic use as agents for treating hypercholesterolemia or atherosclerosis, the compounds of Formulas I or II or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets or transdermal systems are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

Some of the preferred compounds of the present invention are prepared as set forth in Chart I hereof wherein R, $R_1$ and $R_2$ have the meanings defined in Formula I; and Z represents a halogen.

In Route 1, a solution of a halide of the Formula $R_2Z$ in ether is added to a suspension of Li powder in ether heated under reflux. The solution is cooled to 0° C. The resulting lithium compound is then poured into the liquid ethylene oxide precooled to −78° C. The mixture is allowed to warm up to room temperature. After work-up with saturated $NH_4Cl$, the product (3) is extracted with ethyl acetate. The alcohol (3) is oxidized to the acid (4) by Jones reagent ($K_2Cr_2O_7/H_2SO_4$) in acetone at 0° C.

Alternatively, the acid (4) can be arrived at using a method similar to *Org. Syn, Coll.*, 3:557 in which a substituted benzene is chloromethylated followed by replacement of the chlorine with nitrile and subsequent hydrolysis of the nitrile to the acid (4).

The acid (4) is then allowed to react with oxalyl chloride in toluene at room temperature to give acyl chloride (5). Meanwhile, alcohol (6) is treated with chlorosulfonyl isocyanate in refluxing toluene to give Compound 7, which is then hydrolysed with water to give Compound 8. Compounds 5 and 8 are then mixed in THF in the presence of $Et_3N$ at room temperature to give Compound 9. In Route 1A, Compound 9 is also obtained by reacting Compound 7 with $R_2CH_2MgZ$ (15) (commercially available or easily prepared through methods generally known in the art) in THF under reflux. Compound 28 is obtained by subsequently treating Compound 9 (as arrived at by either Route 1 or 1A) with base and then RZ.

Other compounds of the present invention are prepared as set forth in Chart II (Routes 2 and 3), hereof wherein R, $R_1$ and $R_2$ have the meanings defined in Formula I; and Z represents a halogen.

In Route 2, a solution of halide ($R_1CH_2Z$) (14) and thiourea (Compound 24) in absolute ethanol was heated under reflux to give an isothiourea ($R_1CH_2$—S—C(NH)$NH_2$) (25). Chlorine gas was bubbled through a suspended solution of the isothiourea in $H_2O$ at 0° C., followed by $NH_{3(g)}$ to give the sulfonamide ($R_1CH_2SO_2NH_2$) (18). Condensation between the sulfonamide (18) and an acyl chloride ($R_2CH_2COCl$) (5) in THF under $N_2$ in the presence of $Et_3N$ gives an N-acyl sulfonamide (Compound 21). Compound 18 is also allowed to react with Compound 22 (see Route 3 for preparation of Compound 22) in THF in the presence of Et3N at room temperature to give Compound 23. Compound 28 is obtained by subsequently treating Compounds 21 or 23 (as arrived at by Routes 2 or 3, respectively) with a base and then RZ.

The halides RZ, $R_2Z$, and $R_1Z$ used in preparing the compounds of this invention are known in the art or prepared by procedures generally known in the art.

Whereas the preferred compounds of the present invention are prepared as set forth in Charts I and II, it should be understood that the compounds of the present invention can be prepared as set forth generally as follows.

N-acyl sulfamic acid esters (or thioesters) having the formula of Compound 9 in Chart I Route 1 can be prepared by reacting an acyl chloride and a sulfamate having the formula of Compounds 5 and 8, respectively, in Route 1. The resulting ester (or thioester) can optionally be reacted with a base, followed by an aryl halide.

Alternatively, N-acyl sulfamic acid esters (or thioesters) having the formula of Compound 9 in Chart I Route 1A can be prepared by reacting an oxysulfonyl isocyanate and a grignard agent having the formula of Compounds 7 and 15, respectively, in Route 1A. The resulting ester (or thioester) can optionally be reacted with a base, followed by an aryl halide.

N-acyl sulfonamides having the formula of Compound 21 in Chart II Route 2 can be prepared by reacting an acid chloride and a sulfonamide having the formula of Compounds 5 and 18, respectively, in Route 2. The resulting sulfonamide can optionally be reacted with a base, followed by an aryl halide.

N-sulfonyl carbamic acid esters (or thioesters) having the formula of Compound 23 in Chart II Route 3 can be prepared by reacting a sulfonamide and a chloroformate having the formula of Compounds 18 and 22, respectively, in Route 3. The resulting ester (Or thioester) can optionally be reacted with a base, followed by an aryl halide.

EXAMPLES

The following examples illustrate techniques discovered by the inventors for the preparation of the compounds of the present invention. It should be appreciated by those of skill in the art that the techniques disclosed in the examples which follow represent laboratory techniques discovered by the inventors to function well in the practice of the invention, and thus can be considered to constitute preferred modes for this practice. Those of skill in the art should, however, in light of the present disclosure, appreciate that many changes can be made in the specific embodiments which are disclosed and still obtain a like or similar result without departing from the spirit and scope of the invention. In other words, the following examples are given to illustrate particular compositions and methods within the scope of the present invention and are not intended to limit the scope of the present invention.

EXAMPLE 1

Synthesis of sulfamic acid[[2,6-bis(1-methylethyl)phenyl]acetyl]-2,6-bis(1-methylethyl)phenyl ester (a) 2,6-Diisopropylphenylethanol 2,6 diisopropylbromobenzene (see *J. Org. Chem.*, 42(14):2426–2431 (1977) for preparation) (30 g, 124.4 mmol) was added to a suspension of Li powder (1.9 g, 273.6 mmol) in ether (100 mL) heated under reflux, the heating was continued for another 4 hours, cooled, and the mixture was poured into ethylene oxide which was precooled to –78° C. The mixture was warmed slowly to room temperature, saturated $NH_4Cl$ solution was added slowly with caution, the ether layer was separated and washed with brine, dried over $MgSO_4$, filtered, and the solvent was evaporated to dryness. After column chromatography (3:1 hexane:ethyl acetate) pure 2,6-diisopropylphenylethanol was obtained (17 g, 6.3%); NMR ($CDCl_3$): δ 1.2–1.3 (m, 12H), 3.05 (t, 2H), 3.15–3.35 (m, 2H), 3.7–3.8 (t, 2H), 7.1–7.3 (m, 3H) ppm.

(b) 2,6-Diisopropylacetic Acid

Jones reagent (94 mL, 2 M, 188 mmol) was added to a solution of 2,6-diisopropylphenylethanol (19.2 g, 93.05 mmol) in acetone (600 mL) at 0° C. over 2 hours. The mixture was stirred for another 0.5 hour. The reaction mixture was poured into ether (1 L), washed with brine, and the product was extracted by 1N NaOH. The basic extract was acidified with concentrated HCl, the liberated acid was removed by ether extraction (200 mL×5). The combined ether extract was dried over $MgSO_4$, filtered, and then evaporated. The residue was used for the next step without further purification (18.47 g, 90%); NMR ($CDCl_3$): δ 1.15–1.35 (m, 12H), 3.05–3.25 (m, 2H), 3.85 (s, 2H), 7.1–7.35 (m, 3H) ppm.

(c) Sulfamic acid[[2,6-bis(1-methylethyl)phenyl]acetyl]-2,6-bis(1-methylethyl)phenyl ester 2,6-Diisopropylacetic acid (200 mg, 0.91 mmol) and oxalyl chloride (253.9 mg, 2 mmol) were mixed together in 20 mL of toluene at room temperature under $N_2$ with a few drops of DMF as catalyst. The mixture was stirred for 16 hours, the solvent and the excess oxalyl chloride were then removed in vacuo, and the acyl chloride was redissolved in 20 mL of dry THF. 2,6-Diisopropylphenyl sulfamate (257 mg, 1 mmol, see *Phos. and Sulf.*, 19:167 (1984) for preparation) and $Et_3N$ (139 μL, 1 mmol) were added to the solution under $N_2$ and the mixture was stirred at room temperature for 3 hours. The solvent was removed and the residue was distributed between ethyl acetate and 1N HCl. The organic layer was dried over $MgSO_4$, filtered, and evaporated, and the pure product was isolated by column chromatography (1:1 hexane:EtOAc, 300 mg, 72%), mp 166°–168° C.

EXAMPLE 2

Synthesis of sulfamic acid[[2,6-bis(1-methylethyl)phenyl]acetyl]-2,6-bis(1-methylethyl)phenyl ester sodium salt The sodium salt of the title compound of Example 1 was prepared by dissolving the title compound of Example 1 (1 g, 2.18 mmol) in THF (10 mL), and one equivalent of NaH (87 mg, 2.18 mmol) was added to the solution and this was then stirred for 0.5 hour. The solvent was evaporated and product was obtained by trituration with hexane (0.63 g, 60%), mp 242°–244° C.

EXAMPLE 3

Synthesis of sulfamic acid[[2,6-bis(1-methylethyl)phenyl]acetyl]-2,4,6-tris(1-methylethyl)phenyl ester This compound was prepared in the same manner as for the title compound of Example 1, except that 2,6-diisoproplyphenyl sulfamate was replaced with 2,4,6-triisoproplyphenyl sulfamate, mp 152°–155° C.

EXAMPLE 4

Synthesis of sulfamic acid[adamantaneacetyl]-2,6-bis[1-methylethyl]phenyl ester This compound was prepared in the same manner as for the title compound of Example 1, except that 2,6-diisopropylphenylacetyl chloride was replaced with adamantaneacetyl chloride; $^1$H NMR(CDCl$_3$): 1.21 (d, 12H), 1.6–2.0 (m, 15H), 2.15 (s, 2H), 3.4 (m, 2H), 7.15–7.25 (m, 3H) ppm.

EXAMPLE 5

Synthesis of Sulfamic acid[[2,4,6-tris(1-methylethyl)phenyl]acetyl]-2,6-bis(1-methylethyl)phenyl ester (a) 2,4,6-Triisopropylbenzyl alcohol A solution of commercially available 2,4,6-triisopropylbenzoyl chloride (35 g, 131.2 mmol) in 400 mL ether was added slowly to a suspension of lithium aluminum hydride (LAH) (4.89 g, 131.2 mmol) in ether (300 mL) at −15° C. The mixture was slowly warmed to room temperature over 18 hours. Saturated Na$_2$SO$_4$ solution was added slowly and the ether layer was separated, dried over MgSO$_4$, and evaporated to dryness. The compound was used in the next step without further purification; NMR (CDCl$_3$): δ 1.2–1.4 (m, 18H), 2.8–3.0 (m, 1H), 3.3–3.5 (m, 2H), 4.8 (s, 2H), 7.1 (s, 2H) ppm.

(b) 2,4,6-Triisopropylbenzyl bromide

A solution of PBr$_3$ (2.7 g, 10 mmol) in ether (10 mL) was added slowly to a solution of 2,4,6-triisopropylbenzyl alcohol (4.68 g, 20 mmol) in 20 mL of ether at room temperature. The mixture was stirred for 1 hour, 5 mL of absolute EtOH was added, and stirring was continued for another 0.5 hour. The solvent was removed and the residue distributed between EtOAc and saturated Na$_2$CO$_3$. The EtOAc layer was separated, washed with brine, and dried over MgSO$_4$. The solvent was evaporated and the pure product was isolated by column chromatography (100% CH$_2$Cl$_2$, 3.5 g, 59%); NMR (CDCl$_3$): δ 1.2–1.4 (m, 18H), 2.8–3.0 (m, 1H), 3.2–3.45 (m, 2H), 4.7 (s, 2H), 7.04 (s, 2H) ppm.

(c) Sulfamic acid [2,4,6-tris(1-methylethyl)phenyl]acetyl]2,6-bis(1-methylethyl)phenyl ester A solution of 2,4,6 - triisopropylbenzyl bromide (12 g, 40.4 mmol) in dry THF (160 mL) was added to a suspension of Mg powder (1.96 g, 80.8 mmol) (4 hours) in THF (20 mL) heated under reflux. 2,6-Diisopropylphenoxysulfonyl isocyanate (ROSO$_2$NCO) (see *Phos. and Sulf.*, 19:167 (1984) for preparation) (11.45 g, 40.4 mmol) was added neat, and after the addition was completed, the reflux was continued for another 2 hours. The reaction was stirred at room temperature for 16 hours. Saturated NH$_4$Cl and EtOAc were added. The EtOAc layer was separated, dried over MgSO$_4$, filtered, and evaporated to dryness. After purification by column chromatography (4:1 hexane:EtOAc), the compound was isolated as white solid (13.5 g, 67%), mp 178°–180° C.

EXAMPLE 6

Synthesis of sulfamic acid[[2,4,6-tris(1-methylethyl)phenyl]acetyl]-2,6-bis(1-methylethyl)phenyl ester sodium salt This compound was prepared in the same manner as for the title compound of Example 2, except that the title compound of Example 1 was replaced with the title compound of Example 5, mp 250°–252° C.

EXAMPLE 7

Synthesis of sulfamic acid(phenylacetyl)-2,6-bis(1-methylethyl)phenyl ester

This compound was prepared in the same manner as the title compound of Example 5, except that 2,4,6-triisopropylbenzyl magnesium bromide was replaced with benzylmagnesium chloride (commercially available), mp 150°–152° C.

EXAMPLE 8

Synthesis of sulfamic acid[[2,4,6-tris(1-methylethyl)phenyl]acetyl]-2,4,6-tris(1-methylethyl)phenyl ester This compound was prepared in the same manner as the title compound of Example 5, except that 2,6-diisopropylphenoxy sulfonyl isocyanate was replaced with 2,4,6-triisopropylphenoxy sulfonyl isocyanate, mp 178°–180° C.

EXAMPLE 9

Synthesis of 2,6-Bis(1-methylethyl)-N-[[[2,4,6-tris(1-methylethyl)phenyl]methyl]sulfonyl] benzeneacetamide (a) S-2,4,6-Triisopropylbenzyliosthiourea A mixture of 2,4,6-triisopropylbenzyl bromide (6.0 g, 20 mmol) and thiourea (1.536 g, 20.1 mmol) in 180 mL of absolute EtOH was heated under reflux for 3 hours. The reaction was cooled and evaporated. The white powder (7.1 g, 95%) was used for next step without further purification, mp 200°–205° C.

(b) 2,4,6-Triisopropylbenzylsulfonamide

Chlorine gas was bubbled through a suspension of S-2,4,6-triisopropylbenzylisothiourea hydrobromide (2.5 g, 8.56 mmol) in H$_2$O (100 mL) at 0° C. for 1 hour. The solid was extracted into EtOAc (50 mL) and NH$_{3(g)}$ was bubbled through the EtOAc solution at 0° C. for 0.5 hour and the solution was further stirred at room temperature for 2 hours. 2,4,6-Triisopropylbenzylsulfonamide was isolated as white powder (100 mg) by column chromatography (4:1 hexane:EtOAc); NMR (CDCl$_3$): δ 1.2–1.6 (m, 18H), 2.8–3.0 (m, 2H), 3.25–3.4 (m, 2H), 4.75 (s, 2H), 7.0 (s, 2H), ppm.

(c) 2,6-Bis(1-methylethyl)-N-[[[2,4,6-tris(1-methylethyl)phenyl]methyl]sulfonyl]benzeneacetamide A solution of 2,4,6-triisopropylbenzylsulfonamide (100 mg, 0.33 mmol), 2,6-diisopropylphenylacetyl chloride (75 mg, 0.34 mmol), and Et$_3$N (47 µL, 0.34 mmol) in 10 mL THF was stirred at room temperature overnight. The solvent was evaporated and the residue was distributed between ethyl acetate and 0.1N HCl, the organic layer was washed with brine, dried, and evaporated. The pure product (20 mg, 12%) was isolated by column chromatography (4:1 hexane:EtOAc), m/e=499; NMR (CDCl$_3$): δ 7.05–7.4 (m, 5H), 4.25 (s, 2H), 3.95 (s, 2H), 3.45–3.6 (m, 1H), 3.0–3.15 (m, 2H), 2.85–3.0 (m, 2H), 1.05–1.4 (m, 30H) ppm.

EXAMPLE 10

Synthesis of sulfamic acid (decanoyl)-2,6-bis(1-methylethyl)phenyl ester

This compound was prepared in the same manner as for the title compound of Example 1, except that 2,6-diisopropylphenylacetyl chloride was replaced with decanoyl chlo-

EXAMPLE 11

Synthesis of sulfamic acid(dodecanoyl)-2,6-bis(1-methylethyl)phenyl ester

This compound was prepared in the same manner as for the title compound of Example 1, except that 2,6-diisopropylphenylacetyl chloride was replaced with dodecanoyl chloride; $^1$H NMR (DMSO-26): δ 7.09 (s, 3H), 3.65 (heptet, 2H), 2.05 (t, 2H), 1.48–1.15 (m, 18H); 1.10 (d, 6H), 0.86 (t, 3H) ppm.

EXAMPLE 12

Synthesis of sulfamic acid[1-adamantyl(carbonyl)-2,6-bis(1-methylethyl)phenyl ester This compound was prepared in the same manner as for the title compound of Example 1, except that 2,6-diisopropylphenylacetic acid was replaced with 1-adamantecarboxylic acid, mp 165°–167° C.

EXAMPLE 13

Synthesis of sulfamic acid(1-oxo-3,3-diphenylpropyl)-2,6-bis(1-methylethyl)phenyl ester This compound was prepared in the same manner as for the title compound of Example 1, except that 2,6-diisopropylphenylacetic acid was replaced with 3,3-diphenylpropionic acid, mp 149°–152° C.

EXAMPLE 14

Synthesis of sulfamic acid[2,6-dichlorophenyl(acetyl)]-2,6-bis(1-methylethyl)phenyl ester This compound was prepared in the same manner as for the title compound of Example 1, except that 2,6-diisopropylphenylacetic acid was replaced with 2,6-dichlorophenylacetic acid, mp 203°–205° C.

EXAMPLE 15

Synthesis of sulfamic acid trans-[(2-phenylcyclopropyl)carbonyl]-2,6-bis(1-methylethyl)phenyl ester This compound was prepared in the same manner as for the title compound of Example 1, except that 2,6-diisopropylphenylacetic acid was replaced with trans-2-phenylcyclopropylcarboxylic acid, mp 166°–168° C.

EXAMPLE 16

Synthesis of sulfamic acid[2,5-dimethoxyphenyl(acetyl)]-2,6-bis(1-methylethyl)phenyl ester This compound was prepared in the same manner as for the title compound of Example 1, except that 2,6-diisopropylphenylacetyl chloride was replaced with 2,5-dimethoxyphenylacetyl chloride, mp 150°–152° C.

EXAMPLE 17

Synthesis of sulfamic acid[2,4,6-trimethoxyphenyl(acetyl)]-2,6-bis(1-methylethyl)phenyl ester This compound was prepared in the same manner as for the title compound of Example 1, except that 2,6-diisopropylphenylacetic acid was replaced with 2,4,6-trimethoxyphenylacetic acid, mp 159°–163° C.

EXAMPLE 18

Synthesis of sulfamic acid[2,4,6-trimethylphenyl(acetyl)]-2,6-bis(1-methylethyl)phenyl ester This compound was prepared in the same manner as for the title compound of Example 1, except that 2,6-diisopropylphenylacetic acid was replaced with 2,4,6-trimethylphenylacetic acid, mp 159°–161° C.

EXAMPLE 19

Synthesis of sulfamic acid[2-thiophenyl(acetyl)]-2,6-bis(1-methylethyl)phenyl ester This compound was prepared in the same manner as for the title compound of Example 1, except that 2,6-diisopropylphenylacetic acid was replaced with 2-thiopheneacetic acid, mp 133°–136° C.

EXAMPLE 20

Synthesis of sulfamic acid[3-thiophenyl(acetyl)]-2,6-bis(1-methylethyl)phenyl ester This compound was prepared in the same manner as for the title compound of Example 1, except that 2,6-diisopropylphenylacetic acid was replaced with 3-thiopheneacetic acid, mp 136°–138° C.

EXAMPLE 21

Synthesis of sulfamic acid[2-methoxyphenyl(acetyl)]-2,6-bis(1-methylethyl)phenyl ester This compound was prepared in the same manner as for the title compound of Example 1, except that 2,6-diisopropylphenylacetic acid was replaced with 2-methoxyphenylacetic acid, mp 159°–161° C.

EXAMPLE 22

Synthesis of sulfamic acid(oxophenylacetyl)-2,6-bis(1-methylethyl)phenyl ester

This compound was prepared in the same manner as for the title compound of Example 1, except that 2,6-diisopropylphenylacetic acid was replaced with benzoylformic acid, mp 106°–109° C.

EXAMPLE 23

Synthesis of sulfamic acid[2-trifluoromethylphenyl(acetyl)]-2,6-bis(1-methylethyl)phenyl ester This compound was prepared in the same manner as for the title compound of Example 1, except that 2,6-diisopropylphenylacetic acid was replaced with 2-trifluoromethylphenylacetic acid, mp 144°–149° C.

EXAMPLE 24

Synthesis of sulfamic acid(1-oxo-2-phenylpropyl)-2,6-bis(1-methylethyl)phenyl ester This compound was prepared in the same manner as for the title compound of Example 1, except that 2,6-diisopropylphenylacetic acid was replaced with 2-phenylpropionic acid, mp 142°–144° C.

EXAMPLE 25

Synthesis of sulfamic acid(cyclopentylphenylacetyl)-2,6-bis(1-methylethyl)phenyl ester This compound was prepared in the same manner as for the title compound of Example 1, except that 2,6-diisopropylphenylacetic acid was replaced with α-phenylcyclopentanecarboxylic acid, mp 142°–143° C.

EXAMPLE 26

Synthesis of sulfamic acid(cyclohexylacetyl)-2,6-bis(1-methylethyl)phenyl ester

This compound was prepared in the same manner as for the title compound of Example 1, except that 2,6-diisopropylphenylacetic acid was replaced with cyclohexylacetic acid; $^1$H NMR (CDCl$_3$): δ 8.35 (s, 1H), 7.1–7.3 (m, 3H), 3.3–3.45 (m, 2H), 2.35 (d, 2H), 1.55–1.95 (m, 8H), 1.22 (d, 12H), 0.9–1.1 (m, 2H), ppm.

EXAMPLE 27

Synthesis of sulfamic acid(diphenylacetyl)-2,6-bis(1-methylethyl)phenyl ester

This compound was prepared in the same manner as for the title compound of Example 1, except that 2,6-diisopropylphenylacetic acid was replaced with diphenylacetic acid, mp 164°–166° C.

EXAMPLE 28

Synthesis of sulfamic acid(triphenylacetyl)-2,6-bis(1-methylethyl)phenyl ester

This compound was prepared in the same manner as for the title compound of Example 1, except that 2,6-diisopropylphenylacetic acid was replaced with triphenylacetic acid, mp 142°–144° C.

EXAMPLE 29

Synthesis of sulfamic acid[(1,2,3,4-tetrahydro-2-naphthyl)carbonyl]-2,6-bis(1-methylethyl)phenyl ester This compound was prepared in the same manner as for the title compound of Example 1, except that 2,6-diisopropylphenylacetic acid was replaced with 1,2,3,4-tetrahydro-2-naphthoic acid, mp 137°–139° C.

EXAMPLE 30

Synthesis of sulfamic acid[(1-phenylcyclopentyl)carbonyl]-2,6-bis(1-methylethyl)phenyl ester This compound was prepared in the same manner as for the title compound of Example 1, except that 2,6-diisopropylphenylacetic acid was replaced with 1-phenyl-1-cyclopentanecarboxylic acid, mp 149°–152° C.

EXAMPLE 31

Synthesis of sulfamic acid(3-methyl-1-oxo-2-phenylpentyl)-2,6-bis(1-methylethyl)phenyl ester This compound was prepared in the same manner as for the title compound of Example 1, except that 2,6-diisopropylphenylacetic acid was replaced with 3-methyl-2-phenylvaleric acid; $^1$H NMR (CDCl$_3$): δ 8.65 (bs, 1H), 7.36–7.11 (m, 8H), 3.35–3.21 (m, 3H), 2.18 (bs, 1H), 1.73–0.69 (m, 20H), ppm.

EXAMPLE 32

Synthesis of sulfamic acid(1-oxo-2-phenylbutyl)-2,6-bis(1-methylethyl)phenyl ester This compound was prepared in the same manner as for the title compound of Example 1, except that 2,6-diisopropylphenylacetyl chloride was replaced with 2-phenylbutyryl chloride, mp 142°–145° C.

EXAMPLE 33

Synthesis of sulfamic acid(cyclohexylphenylacetyl)-2,6-bis(1-methylethyl)phenyl ester This compound was prepared in the same manner as for the title compound of Example 1, except that 2,6-diisopropylphenylacetic acid was replaced with α-phenylcyclohexanecarboxylic acid, mp 127°–137° C.

EXAMPLE 34

Synthesis of sulfamic acid(1-oxo-2,2-diphenylpropyl)-2,6-bis(1-methylethyl)phenyl ester This compound was prepared in the same manner as for the title compound of Example 1, except that 2,6-diisopropylphenylacetic acid was replaced with 2,2-diphenylpropionic acid, mp 140°–145° C.

EXAMPLE 35

Synthesis of sulfamic
acid[bis-(4-chlorophenyl)acetyl]-2,6-bis(1-
methylethyl)phenyl ester This compound was prepared in the same manner as for the title compound of Example 1, except that 2,6-diisopropylphenylacetic acid was replaced with bis(4-chlorophenyl)acetic acid, mp 175°–176° C.

EXAMPLE 36

Synthesis of sulfamic
acid[(9H-xanthen-9-yl)carbonyl]-2,6-bis(1-
methylethyl)phenyl ester This compound was prepared in the same manner as for the title compound of Example 1, except that 2,6-diisopropylphenylacetic acid was replaced with xanthene-9-carboxylic acid, mp 180°–181° C.

EXAMPLE 37

Synthesis of sulfamic
acid[(9H-fluoren-9yl)carbonyl]-2,6-bis(1-
methylethyl)phenyl ester This compound was prepared in the same manner as for the title compound of Example 1, except that 2,6-diisopropylphenylacetic acid was replaced with 9-fluorenecarboxylic acid, mp 146°–147° C.

EXAMPLE 38

Synthesis of sulfamic
acid(1-oxo-3-phenylpropyl)-2,6-bis(1-
methylethyl)phenyl ester This compound was prepared in the same manner as for the title compound of Example 1, except that 2,6-diisopropylphenylacetic acid was replaced with hydrocinnamic acid, mp 121°–124° C.

EXAMPLE 39

Synthesis of sulfamic
acid[bromo(phenyl)acetyl]-2,6l-bis(1-
methylethyl)phenyl ester This compound was prepared in the same manner as for the title compound of Example 1, except that 2,6-diisopropylphenylacetic acid was replaced with α-bromophenylacetic acid, mp 155°–159° C.

EXAMPLE 40

Synthesis of sulfamic
acid[1-oxo-3-[2,4,6-tris-(1-methylethyl)phenyl]-2-
propenyl]-2,6-bis-(1-methylethyl)phenyl ester (a) 3-[2,4,6-tris(1-methylethyl)phenyl]-2-propenyl carboxylic acid, methyl ester A mixture of methyl acrylate (15.9 mL, 176 mmol) and bis(triphenylphosphine)palladium (II) chloride (0.99 g, 1.4 mmol) in 125 mL dimethylformamide and 125 mL triethylamine was heated to reflux for 1 hour and then 2,4,6-triisopropylbromobenzene (10.0 g, 35 mmol) was added. Reflux was continued for 6 hours and then stirred at room temperature for 16 hours. Partitioned the reaction between water and diethyl ether. The ether layer was dried with $MgSO_4$, filtered, and concentrated to give a brown oil. Chromatography ($SiO_2$, eluant=5% ethyl acetate in hexanes) gave 3.80 g of 3-[2,4,6-tris(1-methylethyl)phenyl]-2-propenyl carboxylic acid, methyl ester as an off-white solid, mp 61°–63° C.

(b) 3-[2,4,6-tris(1-methylethyl)phenyl]-2-propenyl carboxylic acid

Sodium hydroxide (0.23 g, 5.7 mmol) was added to a solution of 3-[2,4,6-tris(1-methylethyl)phenyl]-2-propenyl carboxylic acid, methyl ester (1.5 g, 5.2 mmol) in 100 mL methanol and 10 mL water. Stirred at room temperature for 48 hours and concentrated to dryness. Partitioned the residue between water and diethyl ether. The aqueous layer was acidified with concentrated HCl and extracted with dichloromethane. The organic extract was dried over $MgSO_4$, filtered, and concentrated to give 1.33 g of 3-[2,4,6-tris-(1-methylethyl)phenyl]-2-propenyl carboxylic acid as a white solid, mp 201°–203° C.

(c) Sulfamic acid[1-oxo-3-[2,4,6-tris(1-methylethyl)phenyl]-2-propenyl]-2,6-bis(1-methylethyl)phenyl ester This compound was prepared in the same manner as for the title compound of Example 1, except that 2,6-diisopropylphenylacetic acid was replaced with 3-[2,4,6-tris(1-methylethyl)phenyl]-2-propenyl carboxylic acid, mp 144°–148° C.

EXAMPLE 41

Synthesis of sulfamic
acid[1-oxo-3-[2,4,6-tris(1-methylethyl)phenyl]propyl]-2,6-
bis(1-methylethyl)phenyl ester (a) 3-[2,4,6-tris(1-methylethyl)phenyl]propionic acid, methyl ester 3-[2,4,6-tris(1-methylethyl)phenyl]-2-propenyl carboxylic acid, methyl ester (2.20 g, 7.6 mmol, from Example 40 (a)) was dissolved in 100 mL methanol. 0.5 g of 20% palladium on carbon was added and the mixture was charged with 50 psi of hydrogen gas. After 5 hours at room temperature, the reaction was filtered and concentrated to give 2.37 g of 3-[2,4,6-tris(1-methylethyl)phenyl]propionic acid, methyl ester as an off-white solid, mp 45°–47° C.

(b) 3-[2,4,6-tris(1-methylethyl)phenyl]propionic acid

3-[2,4,6-Tris(1-methylethyl)phenyl]propionic acid, methyl ester (2.12 g, 7.3 mmol) was dissolved in 100 mL methanol and 10 mL water. Sodium hydroxide (0.32 g, 8.0 mmol) was added and the resulting solution was stirred at room temperature for 4 hours. Concentrated in vacuo and partitioned the residue between water and diethyl ether. The aqueous layer was acidified with concentrated HCl and extracted with dichloromethane. The organic extract was dried over $MgSO_4$, filtered, and concentrated to give 1.87 g of 3-[2,4,6-tris(1-methylethyl)phenyl]propionic acid as a white solid, mp 194°–196° C.

(c) Sulfamic acid[1-oxo-3-[2,4,6-tris(1-methylethyl)phenyl]propyl]-2,6-bis(1-methylethyl)phenyl ester This compound was prepared in the same manner as for the title compound of Example 1, except that 2,6-diisopropylphenylacetic acid was replaced with 3-[2,4,6-tris(1-methylethyl)phenyl]propionic acid, mp 138°–141° C.

EXAMPLE 42

Synthesis of sulfamic acid[(acetyloxy)[2,4,6-tris(1-
methylethyl)phenyl]acetyl]-2,6-bis(1-methylethyl)phenyl
ester (a) Acetyloxy[2,4,6-tris(1-methylethyl)phenyl]acetic acid Glyoxylic acid (1.99 g, 27 mmol) and 1,3,5-triisopropylbenzene (5.0 g, 24.5 mmol) were mixed in 30 mL glacial acetic acid and 2 mL concentrated sulfuric acid. The resulting solution was heated to reflux for 5 hours and then stirred at room temperature for 16 hours. The reaction mixture was poured into 100 g ice and the resulting mixture was extracted with diethyl ether. The organic layer was dried over $MgSO_4$, filtered, and concentrated to give an oily solid which was recrystallized from hexanes to give 3.29 g of acetyloxy[2,4,6-tris(1-methylethyl)phenyl]acetic acid, mp 166°–169° C.

(b) [(Acetyloxy)[2,4,6-tris(1-methylethyl)phenyl]acetyl]-2,6-bis(1-methylethyl)phenyl ester This compound was prepared in the same manner as for the title compound of Example 1, except that 2,6-diisopropylphenylacetic acid was replaced with acetyloxy[2,4,6-tris(1-methylethyl)phenyl]acetic acid, mp 140°–146° C.

EXAMPLE 43

Synthesis of sulfamic acid[hydroxy[2,4,6-tris(1-methylethyl)phenyl]acetyl]-2,6-bis(1-methylethyl)phenyl ester

[(Acetyloxy)[2,4,6-tris(1-methylethyl)phenyl]acetyl]-2,6-bis(1-methylethyl)phenyl ester (1.50 g, 2.7 mmol) was dissolved in 75 mL methanol and 25 mL water. Sodium hydroxide (0.22 g, 5.5 mmol) was added and the resulting solution was stirred at room temperature for 16 hours. Concentrated in vacuo, redissolved the residue in water, acidified to pH 4.0 with concentrated HCl and extracted with diethyl ether. The organic extract was dried over $MgSO_4$, filtered, and concentrated to give an oil. Triturated with hexanes to give 0.56 g of sulfamic acid [hydroxy[2,4,6-tris(1-methylethyl)phenyl]acetyl]-2,6-bis(1-methylethyl)phenyl ester, mp 96°–101° C.

EXAMPLE 44

Synthesis of sulfamic acid[fluoro[2,4,6-tris(1-methylethyl)phenyl]acetyl]-2,6-bis(1-methylethyl)phenyl ester

[Hydroxy[2,4,6-tris(1-methylethyl)phenyl]acetyl]-2,6-bis(1-methylethyl)phenyl ester (0.73 g, 1.4 mmol) was dissolved in 20 mL dichloromethane and added dropwise to a solution of diethylaminosulfur trifluoride (0.19 mL, 1.4 mmol) in 10 mL dichloromethane at −8° C. Gradually warmed to room temperature and stirred for 16 hours. Concentrated in vacuo and partitioned the residue between water and ethyl acetate. The organic extract was dried over $MgSO_4$, filtered, and concentrated to give a yellow oil. Triturated with hexanes to give 0.39 g of sulfamic acid [fluoro[2,4,6-tris(1-methylethyl)phenyl]acetyl]-2,6-bis(1-methylethyl)phenyl ester, mp 130°–132° C.

EXAMPLE 45

Synthesis of sulfamic acid(3-methyl-1-oxo-2-phenylpentyl)-2,6-bis(1-methylethyl)phenyl ester sodium salt This compound was prepared in the same manner as for the title compound of Example 2, except that the title compound of Example 1 was replaced with the title compound of Example 31, mp 275°–277° C.

EXAMPLE 46

Synthesis of sulfamic acid[[2,4,6-tris(1-methylethyl)phenoxy]acetyl]-2,6-bis(1-methylethyl)phenyl ester (a) [2,4,6-tris(1-methylethyl)phenoxy]acetic acid A solution of 2,4,6-triisopropylphenol (4.0 g, 18 mmol) in 50 mL tetrahydrofuran was added dropwise to a suspension of sodium hydride (1.52 g, 38 mmol) in 25 mL tetrahydrofuran. The resulting pale green suspension was stirred for 30 minutes before a solution of bromoacetic acid (2.52 g, 18 mmol) in 50 mL tetrahydrofuran was added dropwise. The resulting thick suspension was stirred for 16 hours and then concentrated in vacuo. The residue was partitioned between 1N HCl and dichloromethane, the organic extract was dried over $MgSO_4$, filtered, and concentrated to give a yellow solid. Recrystallized from hexanes to give 3.1 g of [2,4,6-tris(1-methylethyl)phenoxy]acetic acid, mp 105°–108° C.

(b) Sulfamic acid[[2,4,6-tris(1-methylethyl)phenoxy]acetyl]-2,6-bis(1-methylethyl)phenyl ester This compound was prepared in the same manner as for the title compound of Example 1, except that 2,6-diisopropylphenylacetic acid was replaced with [2,4,6-tris(1-methylethyl)phenoxy]acetic acid, mp 126°–128° C.

EXAMPLE 47

Synthesis of sulfamic acid[[2,6-bis(1-methylethyl)phenoxy]acetyl]-2,6-bis(1-methylethyl)phenyl ester This compound was prepared in the same manner as for the title compound of Example 46, except that 2,4,6-triisopropylphenol was replaced with 2,6-diisopropylphenol, mp 108°–110° C.

EXAMPLE 48

Synthesis of sulfamic acid[[2,4,6-tris(1-methylethyl)phenyl]acetyl]-2,6-bis(phenyl)phenyl ester (a) 2,6-Bis(phenyl)phenyl sulfamate A solution of chlorosulfonyl isocyanate (5.57 mL, 64 mmol) in 50 mL toluene was added dropwise to a solution of 2,6-diphenylphenol (15.0 g, 61 mmol) in 200 mL toluene at 50° C. The resulting white suspension was heated to reflux for 16 hours. Concentrated in vacuo and carefully partitioned the residue between water and diethyl ether. The ether layer was dried over $MgSO_4$, filtered, and concentrated to give an off-white solid. Recrystallized from hexanes to give 2,6-bis(phenyll)phenyl sulfamate as a white solid, mp 145°–147° C.

(b) Sulfamic acid [[2,4,6-tris(1-methylethyl)phenyl]acetyl]-2,6-bis(phenyl)phenyl ester This compound was prepared in the same manner as for the title compound of Example 1, except that 2,6-diisopropylphenyl sulfamate was replaced with 2,6-bis(phenyl)phenyl sulfamate, mp 129°–132° C.

CHART I
(R, R₁, and R₂ have the meanings defined in Formula I;
and Z represents a halogen)
Route 1
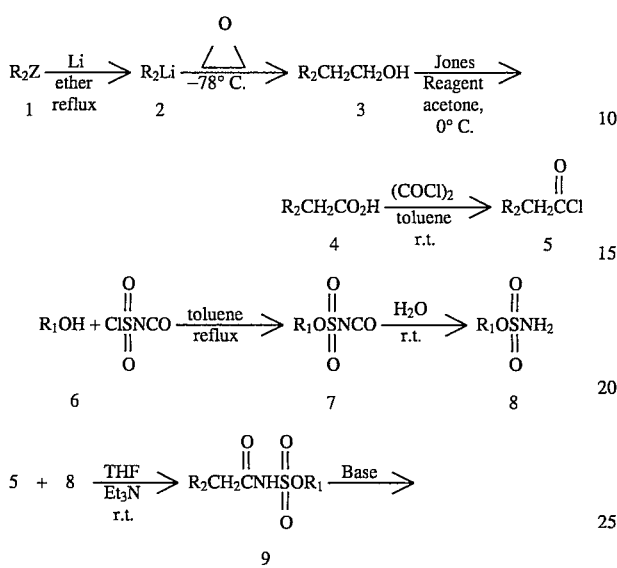
Route 1A
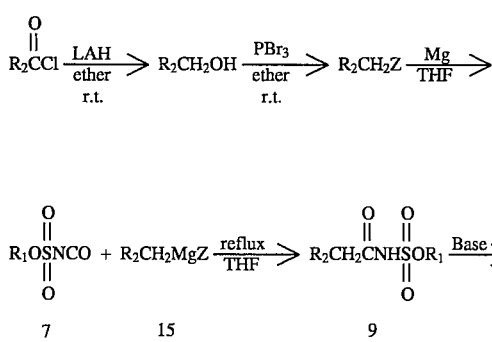
Route 1B
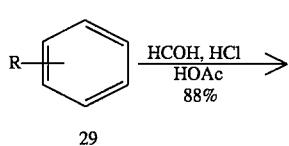
-continued
CHART I
(R, R₁, and R₂ have the meanings defined in Formula I;
and Z represents a halogen)
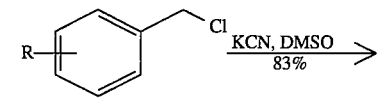
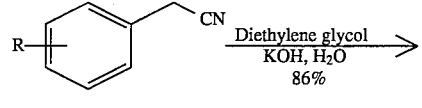
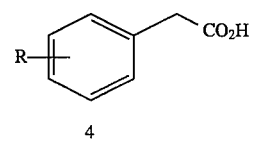
CHART II
(R, R₁, and R₂ have the meanings defined in Formula I;
and Z represents a halogen)
Route 2
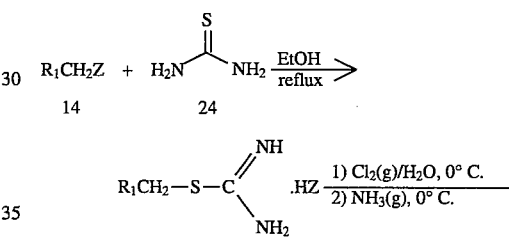
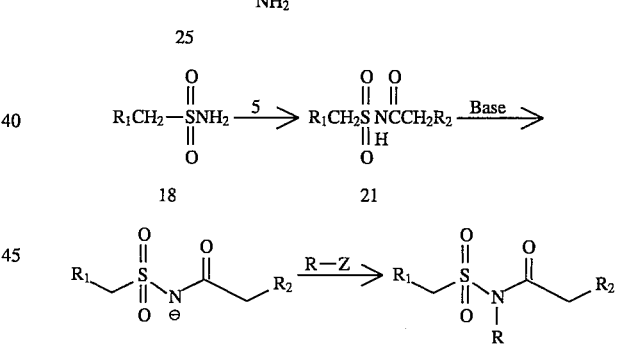
Route 3
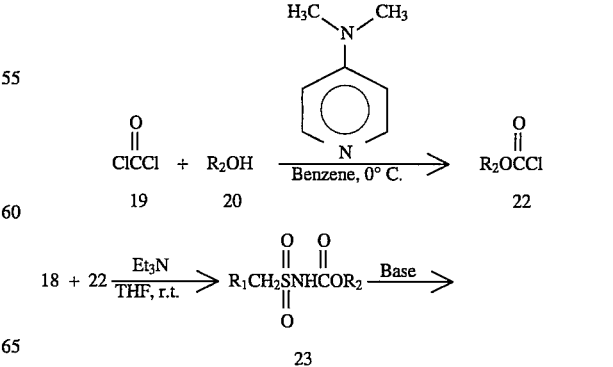

-continued
CHART II
(R, R$_1$, and R$_2$ have the meanings defined in Formula I; and Z represents a halogen)

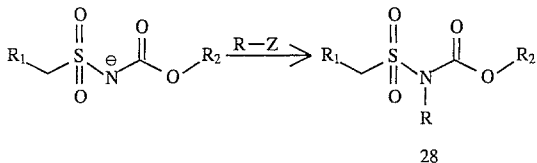

We claim:

1. A compound of the formula

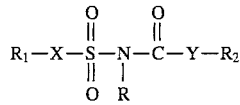

or a pharmaceutically acceptable salt thereof wherein:

X is oxygen;

Y is (CR'R")$_n$ wherein n is an integer of from 1 to 4 and R' and R" are each independently hydrogen, alkyl, alkoxy, halogen, hydroxy, acyloxy, cycloalkyl, phenyl optionally substituted or R' and R" together form a spirocycloalkyl or a carbonyl;

R is hydrogen, a straight or branched alkyl of from 1 to 8 carbon atoms or benzyl;

R$_1$ and R$_2$ are each independently selected from (a) phenyl or phenoxy each of which is unsubstituted or is substituted with 1 to 5 substituents selected from
  phenyl,
  an alkyl group having from 1 to 6 carbon atoms and which is straight or branched,
  an alkoxy group having from 1 to 6 carbon atoms and which is straight or branched;
  phenoxy,
  hydroxy,
  fluorine,
  chlorine,
  bromine,
  nitro,
  trifluoromethyl,
  —COOH,
  —COOalkyl wherein alkyl has from 1 to 4 carbon atoms and is straight or branched,
  —(CH$_2$)$_p$NR$_3$R$_4$ wherein p is zero or one, and each of R$_3$ and R$_4$ is selected from hydrogen or a straight or branched alkyl group having 1 to 4 carbon atoms;

(b) 1- or 2-naphthyl unsubstituted or substituted with from 1 to 3 substituents selected from
  phenyl,
  an alkyl group having from 1 to 6 carbon atoms and which is straight or branched,
  an alkoxy group having from 1 to 6 carbon atoms and which is straight or branched;
  hydroxy,
  phenoxy,
  fluorine,
  chlorine,
  bromine,
  nitro,
  trifluoromethyl,
  —COOH,
  —COOalkyl wherein alkyl has from 1 to 4 carbon atoms and is straight or branched,
  —(CH$_2$)$_p$NR$_3$R$_4$ wherein p, R$_3$ and R$_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms.

2. A compound of claim 1 wherein R$_1$ is phenyl.

3. A compound of claim 2 wherein R$_1$ is phenyl disubstituted in the 2,6-positions.

4. A compound of claim 1 wherein R$_2$ is phenyl.

5. A compound of claim 4 wherein R$_2$ is phenyl disubstituted in the 2,6-positions.

6. A compound of claim 1 wherein each of R$_1$ and R$_2$ is phenyl.

7. A compound of claim 6 wherein each phenyl is disubstituted in the 2,6-positions.

8. A compound of claim 1 wherein R$_1$ is phenyl disubstituted in the 2,6-positions and R$_2$ is phenyl trisubstituted in the 2,4,6-positions.

9. A compound of claim 1 wherein R$_1$ is 2,6-bis(1-methylethyl)phenyl and R$_2$ is 2,6-bis(1-methylethyl)phenyl or 2,4,6-tris(1-methylethyl)phenyl.

10. A compound of claim 1 wherein R$_1$ is phenyl or phenyl disubstituted in the 2,6-positions, wherein R$_2$ is phenyl or is phenyl disubstituted in the 2,6-positions, wherein each of R$_1$ and R$_2$ is phenyl, wherein each phenyl is disubstituted in the 2,6-position, wherein R$_1$ is phenyl disubstituted in the 2,6-positions and R$_2$ is phenyl trisubstituted in the 2,4,6-positions, wherein R$_1$ is 2,6-bis(1-methylethyl)phenyl and R$_2$ is 2,6-bis(1-methylethyl)phenyl or 2,4,6-tris(1-methylelthyl)phenyl, wherein one of R$_1$ and R$_2$ is the group $$-(CH_2)_t-\underset{\underset{R_6}{|}}{\overset{\overset{R_5}{|}}{C}}-(CH_2)_w-R_7$$

wherein t is zero or 1 to 4; w is zero or 1 to 4 with the proviso that the sum of t and w is not greater than 5; R$_5$ and R$_6$ are each independently selected from hydrogen or alkyl having from 1 to 6 carbon atoms, or when R$_5$ is hydrogen, R$_6$ can be selected from the groups defined for R$_7$; and R$_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —(CH$_2$)$_p$NR$_3$R$_4$ wherein P, R$_3$ and R$_4$ have the meanings defined above.

11. A compound according to claim 1 wherein

X is oxygen;

Y is (CR'R")$_n$ wherein n is an integer of from 1 to 4 and R' and R" are each independently hydrogen, straight or branched alkyl of from 1 to 6 carbons, optionally substituted phenyl, halogen, hydroxy, alkoxy, acyloxy, cycloalkyl, or R' and R" taken together form a carbonyl or a spirocycloalkyl group of from 3 to 10 carbons;

R is hydrogen;

R$_1$ is phenyl optionally substituted, straight or branched alkyl of from 1 to 10 carbon atoms, cycloalkyl of from 3 to 10 carbon atoms;

R$_2$ is phenyl optionally substituted, straight or branched alkyl of from 1 to 10 carbon atoms, cycloalkyl of from 3 to 8 carbon atoms, phenoxy optionally substituted.

12. A compound according to claim 1 wherein
X is oxygen;
Y is (CR'R")$_n$ wherein n is an integer of from 1 to 2;
R is hydrogen;
R$_1$ is optionally substituted phenyl;
R$_2$ is optionally substituted phenyl or phenoxy, straight or branched alkyl of from 1 to 10 carbons, or cycloalkyl of from 3 to 10 carbons;
R' and R" are each independently hydrogen, straight or branched alkyl of from 1 to 6 carbons, optionally substituted phenyl, halogen, hydroxy, alkoxy, acyloxy, cycloalkyl, or R' and R" taken together form a carbonyl or a spirocycloalkyl.

13. A compound of claim 1 selected from:
Sulfamic acid (phenylacetyl)-2,6-bis(1-methylethyl)phenyl ester,
Sulfamic acid[[2,6-bis(1-methylethyl)phenyl]acetyl]-2,6-bis(1-methylethyl)phenyl ester,
Sulfamic acid [[2,4,6-tris(1-methylethyl)phenyl]acetyl-2,4,6-tris(1-methylethyl)phenyl ester,
Sulfamic acid[[2,6-bis(1-methylethyl)phenyl]acetyl]-2,4,6-tris(1-methylethyl)phenyl ester,
Sulfamic acid[adamantaneacetyl]-2,6-bis[1-methylethyl)phenyl ester,
Sulfamic acid[[2,6-bis(1-methylethyl)phenyl]acetyl]-2,6-bis(1-methylethyl)phenyl ester-sodium salt,
Sulfamic acid[[2,4,6-tris(1-methylethyl)phenyl]acetyl]-2,6-bis(1-methylethyl)phenyl ester-sodium salt,
Sulfamic acid (decanoyl)-2,6-bis-(1-methylethyl)phenyl ester,
Sulfamic acid (dodecanoyl)-2,6-bis-(1-methylethyl)phenyl ester,
2,6-Bis(1-methylethyl)-N-[[[2,4,6-tris(1-methylethyl)phenyl]methyl]sulfonyl]benzeneacetamide,
2,6-Bis(1-methylethyl)-N-[[[2,4,6-tris(1-methylethyl)phenyl]methyl]sulfonyl]benzeneacetamide-sodium salt.
2,6-Bis(1-methylethyl)phenyl[[[2,4,6-tris(1-methylethyl)phenyl]methyl]sulfonyl]carbamate,
2,6-Bis(1-methylethyl)phenyl[[[2,4,6-tris(1-methylethyl)phenyl]methyl]sulfonyl]carbamate-sodium salt,
Sulfamic acid (1-oxo-3,3-diphenylpropyl)-2,6-bis(1-methylethyl)phenyl ester,
Sulfamic acid [2,6-dichlorophenyl(acetyl)]-2,6-bis(1-methylethyl)phenyl ester,
Sulfamic acid [2,6-dichlorophenyl(acetyl)]-2,6-bis(1-methylethyl)phenyl ester,
Sulfamic acid trans-[(2-phenylcyclopropyl)carbonyl]-2,6-bis(1-methylethyl)phenyl ester,
Sulfamic acid [2,5-dimethoxyphenyl(acetyl)]-2,6-bis(1-methylethyl)phenyl ester,
Sulfamic acid [2,4,6-trimethoxyphenyl(acetyl)]-2,6-bis(1-methylethyl)phenyl ester,
Sulfamic acid [2,4,6-trimethylphenyl(acetyl)]-2,6-bis(1-methylethyl)phenyl ester,
Sulfamic acid [2-thiophenyl(acetyl)]-2,6-bis(1-methylethyl)phenyl ester,
Sulfamic acid [3-thiophenyl(acetyl)]-2,6-bis(1-methylethyl)phenyl ester,
Sulfamic acid [2-methoxyphenyl(acetyl)]-2,6-bis(1-methylethyl)phenyl ester,
Sulfamic acid (oxophenylacetyl)-2,6-bis(1-methylethyl)phenyl ester,
Sulfamic acid [2-trifluoromethylphenyl(acetyl)]-2,6-bis(1-methylethyl)phenyl ester,
Sulfamic acid (1-oxo-2-phenylpropyl)-2,6-bis(1-methylethyl)phenyl ester,
Sulfamic acid (cyclopentylphenylacetyl)-2,6-bis(1-methylethyl)phenyl ester,
Sulfamic acid (cyclohexylacetyl)-2,6-bis(1-methylethyl)phenyl ester,
Sulfamic acid (diphenylacetyl)-2,6-bis(1-methylethyl)phenyl ester,
Sulfamic acid (triphenylacetyl)-2,6-bis(1-methylethyl)phenyl ester,
Sulfamic acid [(11-phenylcyclopentyl)carbonyl]-2,6-bis(1-methylethyl)phenyl ester,
Sulfamic acid (3-methyl-1-oxo-2-phenylpentyl)-2,6-bis(1-methylethyl)phenyl ester,
Sulfamic acid (1-oxo-2-phenylbutyl)-2,6-bis(1-methylethyl)phenyl ester,
Sulfamic acid (cyclohexylphenylacetyl)-2,6-bis(1-methylethyl)phenyl ester,
Sulfamic acid (1-oxo-2,2-diphenylpropyl)-2,6-bis(1-methylethyl)phenyl ester,
Sulfamic acid [(9H-fluoren-9-yl)carbonyl]-2,6-bis(1-methylethyl)phenyl ester,
Sulfamic acid (1-oxo-3-phenylpropyl)-2,6-bis(1-methylethyl)phenyl ester,
Sulfamic acid [1-oxo-3-[2,4,6-tris(1-methylethyl)phenyl-2-propenyl]-2,6-bis(1-methylethyl)phenyl ester,
Sulfamic acid [1-oxo-3-[2,4,6-tris(1-methylethyl)phenyl]propyl]-2,6-bis(1-methylethyl)phenyl ester,
Sulfamic acid [(acetyloxy)[2,4,6-tris(1-methylethyl)phenyl]acetyl]-2,6-bis(1-methylethyl)phenyl ester,
Sulfamic acid [hydroxy[2,4,6-tris(1-methylethyl)phenyl]acetyl]-2,6-bis(1-methylethyl)phenyl ester,
Sulfamic acid [fluoro[2,4,6-tris(1-methylethyl)phenyl]acetyl]-2,6-bis(1-methylethyl)phenyl ester,
Sulfamic acid (3-methyl-1-oxo-2-phenylpentyl)-2,6-bis(1-methylethyl)phenyl ester sodium salt,
Sulfamic acid [[2,4,6-tris(1-methylethyl)phenoxy]acetyl]-2,6-bis(1-methylethyl)phenyl ester,
Sulfamic acid [[2,6-bis(1-methylethyl)phenoxy]acetyl]-2,6-bis(1-methylethyl)phenyl ester, and
Sulfamic acid [[2,4,6-tris(1-methylethyl)phenyl]acetyl]-2,6-bis(phenyl)phenyl ester.

14. A pharmaceutical composition for regulating plasma cholesterol concentrations comprising an effective amount of a compound of formula $$R_1-X-\overset{\overset{O}{\|}}{\underset{\underset{O}{\|}}{S}}-\underset{R}{N}-\overset{\overset{O}{\|}}{C}-Y-R_2 \qquad I$$

or a pharmaceutically acceptable salt thereof wherein:
X is oxygen; Y is (CR'R")$_n$ wherein n is an integer of from 1 to 4 and R' and R" are each independently hydrogen, alkyl, alkoxy, halogen, hydroxy, acyloxy, cycloalkyl, phenyl optionally substituted or R' and R" together form a spirocycloalkyl or a carbonyl;
R is hydrogen, a straight or branched alkyl of from 1 to 8 carbon atoms or benzyl;
R$_1$ and R$_2$ are each independently selected from
(a) phenyl or phenoxy each of which is unsubstituted or is substituted with 1 to 5 substituents selected from phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine
nitro,
trifluoromethyl,
—COOH,
—COOalkyl wherein alkyl has from 1 to 4 carbon atoms and is straight or branched,
—(CH$_2$)$_p$NR$_3$R$_4$ wherein p is zero or one, and each of R$_3$ and R$_4$ is selected from hydrogen or a straight or branched alkyl group having 1 to 4 carbon atoms;

(b) 1- or 2-naphthyl unsubstituted or substituted with from 1 to 3 substituents selected from
phenyl,
an alkyl group having from 1 to 6 carbon atoms and which is straight or branched,
an alkoxy group having from 1 to 6 carbon atoms and which is straight or branched;
hydroxy,
phenoxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p, R$_3$ and R$_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms and a pharmaceutically acceptable carrier.

15. A method of treating hypercholesterolemia comprising adminsitering to a patient a therapeutically effective amount of a compound of formula

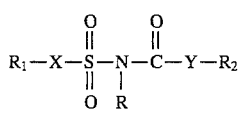

or a pharmaceutically acceptable salt thereof wherein:
X is oxygen; Y is (CR'R'')$_n$ wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl;

R is hydrogen, a straight or branched alkyl of from 1 to 8 carbon atoms or benzyl;

R$_1$ and R$_2$ are each independently selected from (a) phenyl or phenoxy each of which is unsubstituted or is substituted with 1 to 5 substituents selected from
phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p is zero or one, and each of R$_3$ and R$_4$ is selected from hydrogen or a straight or branched alkyl group having 1 to 4 carbon atoms;

(b) 1- or 2-naphthyl unsubstituted or substituted with from 1 to 3 substituents selected from
phenyl,
an alkyl group having from 1 to 6 carbon atoms and which is straight or branched,
an alkoxy group having from 1 to 6 carbon atoms and which is straight or branched;
hydroxy,
phenoxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p, R$_3$ and R$_4$ have the meanings defined above;

(c) arylalkyl;

(d) a straight or branched alkyl chain having from 1 to 20 carbon atoms and which is saturated or contains from 1 to 3 double bonds; or (e) adamantyl or a cyclcoalkyl group having wherein the cycloalkyl moiety has from 3 to 6 carbon atoms.

16. A method of treating atherosclerosis comprising adminsitering to a patient a therapeutically effective amount of a compound of formula

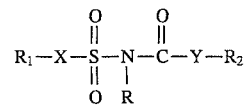

or a pharmaceutically acceptable salt thereof wherein:
X is oxygen; Y is (CR'R'')$_n$ wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl;

R is hydrogen, a straight or branched alkyl of from 1 to 8 carbon atoms or benzyl;

R$_1$ and R$_2$ are each independently selected from (a) phenyl or phenoxy each of which is unsubstituted or is substituted with 1 to 5 substituents selected from
phenyl,
an alkyl group having from 1 to 6 carbon atoms and which is straight or branched,
an alkoxy group having from 1 to 6 carbon atoms and which is straight or branched;
phenoxy,
hydroxy, fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p is zero or one, and each of R$_3$ and R$_4$ is selected from hydrogen or a straight or branched alkyl group having 1 to 4 carbon atoms;

(b) 1- or 2-naphthyl unsubstituted or substituted with from 1 to 3 substituents selected from
phenyl,
an alkyl group having from 1 to 6 carbon atoms and which is straight or branched,
an alkoxy group having from 1 to 6 carbon atoms and which is straight or branched,
hydroxy,
phenoxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p, R$_3$ and R$_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms.

17. A compound named sulfamic acid[[2,4,6-tris(1-methylethyl)phenyl]acetyl-2,6-bis(1-methylethyl)phenyl ester.

* * * * *